(12) United States Patent
Uhlemann

(10) Patent No.: US 6,360,118 B1
(45) Date of Patent: Mar. 19, 2002

(54) DIAGNOSTIC APPARATUS WITH RADIO LINK

(76) Inventor: Gisela Uhlemann, Am Mühlenberg 7, D-45721 Haltern (DE)

( * ) Notice: Subject to any disclaimer, the term of this patent is extended or adjusted under 35 U.S.C. 154(b) by 0 days.

(21) Appl. No.: 09/426,164

(22) Filed: Oct. 22, 1999

(30) Foreign Application Priority Data

Oct. 23, 1998 (DE) .......................................... 198 49 123

(51) Int. Cl.⁷ ............................................ A61B 5/0402
(52) U.S. Cl. ..................................................... 600/509
(58) Field of Search ........................ 128/903; 600/908, 600/909, 523, 525; 607/32, 60

(56) References Cited

FOREIGN PATENT DOCUMENTS

| | | |
|---|---|---|
| DE | 19707681 | 5/1998 |
| DE | 19825898 | 12/1998 |
| WO | WO 97/25100 | 7/1997 |

*Primary Examiner*—William E. Kamm
(74) *Attorney, Agent, or Firm*—Kilpatrick Stockton LLP

(57) ABSTRACT

This invention relates to a diagnostic apparatus, particularly a cardiac diagnostic apparatus, with transmit-receive electronics, eg., in the form of a mobile telephone provided in the housing (2). When operating the apparatus to record electrical body signals, at least the transmit function and, where appropriate, other functions not serving for measurement are disconnected in order to avoid endangerment of persons carrying, e.g., a pacemaker. For example, the electrodes (4,8,12) in a first condition of the diagnostic apparatus are not open, and, as a result of uncovering (5,9,13) at least one electrode (4,8,12), at least the transmit function and, where appropriate, other function not serving for measurement are disconnected.

3 Claims, 2 Drawing Sheets

DIAGNOSTIC APPARATUS WITH RADIO LINK

DESCRIPTION

This invention relates to a diagnostic apparatus, particularly a cardiac diagnostic apparatus, with a housing, a power supply unit provided in the housing, a transmit-receive unit provided at the housing, and electrodes for application to the body and measurement by recording of electrical body signals.

The cardiac diagnostic apparatus of the class specified is known from DE-PS 197 07 681 (C1). With the known apparatus, by means of the electrodes which are fixed (permanently) to the rear of the apparatus, electrical body signals, for example, ECG signals, are recorded and transmitted via a mobile telephone provided in the same housing, for example, a cellular phone, to a remote location. Said remote location can, for example, be a hospital, an emergency call station or the like.

However, it is obvious that the radio signals, above all, those which the apparatus itself transmits, can put at risk the lives of patients carrying an implanted pacemaker. For example, it is known that mobile telephones may not be used in aircraft or anywhere in the vicinity of sensitive electronics.

It is the task of the present invention to so improve a generic diagnostic apparatus that endangerment of the patient is avoided to the greatest extent possible.

The foregoing task is achieved in that, when operating the apparatus to record electrical body signals, at least the transmit function and, where appropriate, other function not serving for the measurement can be disconnected.

The solution in accordance with the invention particularly has the following advantages:

This type of diagnostic apparatus is particularly used in patients with existing cardiac injury. Such patients frequently carry an implanted pacemaker (globally ca. 1 million), which often, especially in emergencies, is overlooked. In a critical moment, patients may possibly not point this out or are unable to do so because of their condition. Above all, pacemakers are prone to considerable interference due to the transmit-receive electronics of mobile telephones, especially when using the diagnostic apparatus in close proximity to the heart, as this possibly may trigger dangerous cardiac rhythm disorders. This can be avoided in that, when placing the apparatus in a condition ready for measuring, the send-receive equipment is automatically disabled in accordance with the invention.

Further, the steps may be, e.g., switching the display field to measurement, the actuation of a measurement key or the like.

Particularly preferred are electrodes (as a rule 3–5 electrodes) in a first condition of the diagnostic apparatus which are not open (i.e., they are covered, for example), and by uncovering at least one electrode, this will disable at least the transmit function and, where appropriate, other functions not serving for the measurement Particularly preferred are electrodes covered by an overall or individual cover, the removal of which at least disables the transmit function, and, where appropriate, other functions not serving for the measurement Such a cover easily makes it evident that, in order to use the apparatus as a diagnostic apparatus, an action must be performed. This action then disables the communication function of the apparatus (for instance, by means of the microswitch connected to the cap or covers), while in case of several covers, the removal of one cover suffices to disable said function.

Further, the connection of a patient cable is understood as a corresponding activation of the apparatus for measurement.

In the following, the invention is explained in detail by means of preferred embodiment examples and by reference to the attached drawings to which particular reference is made due to their great clarity and clear arrangement.

Figure 1:
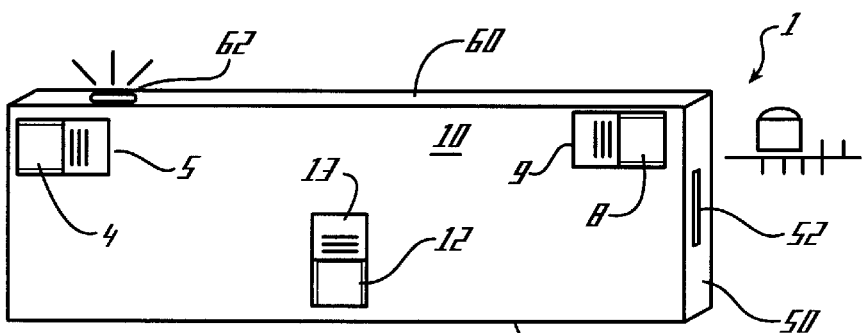
FIG. 1 shows the rear of the diagnostic apparatus in accordance with the invention with three electrodes and their covers which can be opened, said apparatus being in an open condition.

FIG. 1 shows a face 10 (rear) of the housing 2 of the diagnostic apparatus, which overall is designated as 1. The diagnostic apparatus is preferably used as a cardiac diagnostic apparatus for measuring electrical surface signals for determining the cardiac function, but may also be used for measuring cerebral currents, as is known from DE-C-36 36 996. However, this requires the measured electrical signals to be amplified 1000 times compared with the cardiac diagnostic apparatus described. Specifically, during this operation, it is absolutely essential that no interferences are caused by external signals. At the rear 10, electrodes, in the embodiment example, three electrodes, 4, 8, and 12, must be provided at the greatest possible distance. The electrodes, however, may also be removable in order to achieve a greater distance between the measurement points, as compared with patent application No. P 196 02 347.5-35 of the same applicant.

Each of the ECG recording electrodes 4, 8, and 12 is covered by an accompanying cover, in the present case by a sliding cover 5 or 9 or 13 which is hinged at one side. However, for example, spring covers may also be used.

The opening of the sliding covers 5 or 9 or 13 individually disables the function of the apparatus 1, generally all functions not required for measurement, which, e.g., could interfere with a pacemaker. In addition, the ECG electrode is preferably pushed upward and there can preferably be stopped, so that said electrode can be applied to the body more easily.

Figure 2:
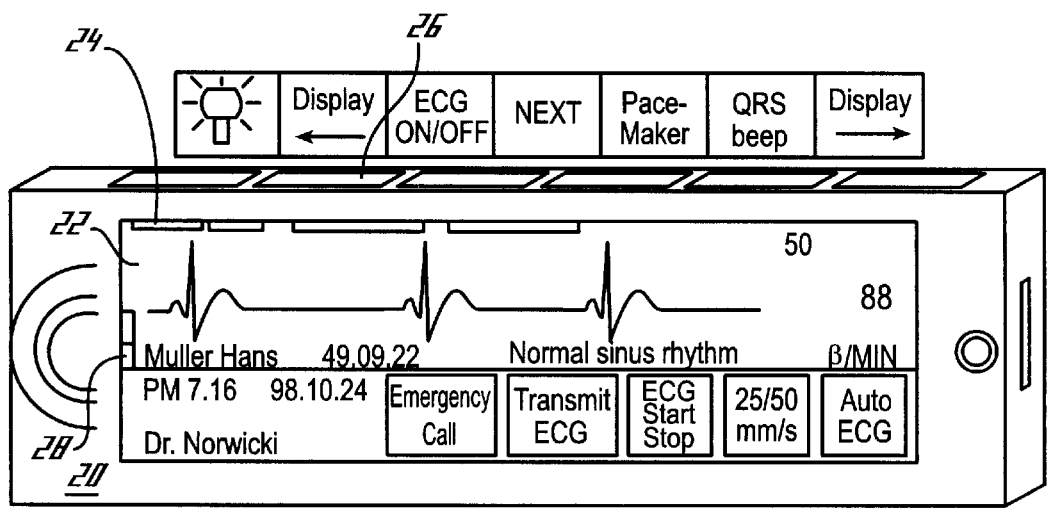
FIG. 2 shows the front of the apparatus in accordance with the invention in measuring condition, with the accompanying control keys and display field, as well as a long, narrow side with the accompanying control keys which are developed as touch keys.

FIG. 2 shows the face 20 of the apparatus 1 located opposite the side 6, which in the present case is designed not only as a general mobile telephone, but also as a special design, a so-called "physician ECG handy," for a physician.

Figure 2A:
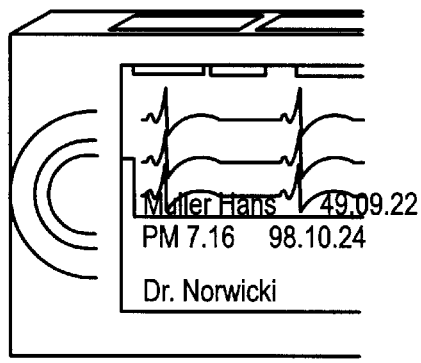

The display field 22, for instance, shows the patient data (name, date of birth), e.g., entered by a patient card or by any other means, as well as the graphic chart of the ECG, which can be recorded and presented as a single or tri-channel recording (the latter is shown in FIG. 2a). Further, right from the start, the name of the attending physician, as well as date and time, can be entered, as is shown in the preferred embodiment example. The heart rate is shown in digits (in the example here: "88").

At its face 20, the apparatus is provided with a generally known "Notruf [emergency call]" key, in this case indicated in the display field of the ECG function, and an "EKG/senden [ECG transmit]" key, which, according to the invention, however, functions only after the electrodes are covered. If appropriate, said apparatus can also be so designed that, e.g., the emergency call key effects a call transmission even when the electrodes are uncovered.

Depressing the "EKG/senden" key transmits the ECG in the ECG memory 24, e.g., to the practice of the attending physician. The "EKG/Start/Stop" key triggers the measurement, with the "25/50 mm/s" key making it possible to switch to another recording speed. The recording speed can also be displayed as shown on the display field 22 at the top right.

The "Auto EKG" key is used when, e.g., an ECG is to be recorded with various leads. A patient cable (not shown) is plugged into the tip jack 52 at the short, narrow side 50 of the housing 2. When using a patient cable, the function is automatically disabled as soon as the patient cable is plugged into the apparatus (52). When using a patient cable, the regular ECG (according to Einthoven I, II, III, Goldberg aVR, aVL, aVF and Wilson V1–6) can be automatically recorded and stored in the apparatus. Connecting the patient cable has the same effect as opening the sliding covers 5 or 9 or 13, i.e., the radio electronics of the apparatus 1 are disconnected.

FIG. 2 shows a section of a top view of the long, narrow side 30 of the housing 2 of the apparatus 1. The "Next" key releases the next memory (e.g., 26 after 24), thus enabling the recording of EKGs of the same patient or EKGs of different patients separately. The keys "Display/←" and "Display/→" allow the subsequent viewing of the stored ECG data.

The key marked with the lamp symbol enables to switch on the preferred installed diagnostic lamp 62, which is provided on the other long, narrow side 60, and may be used, for example, to check papillary reflexes.

Figure 3:
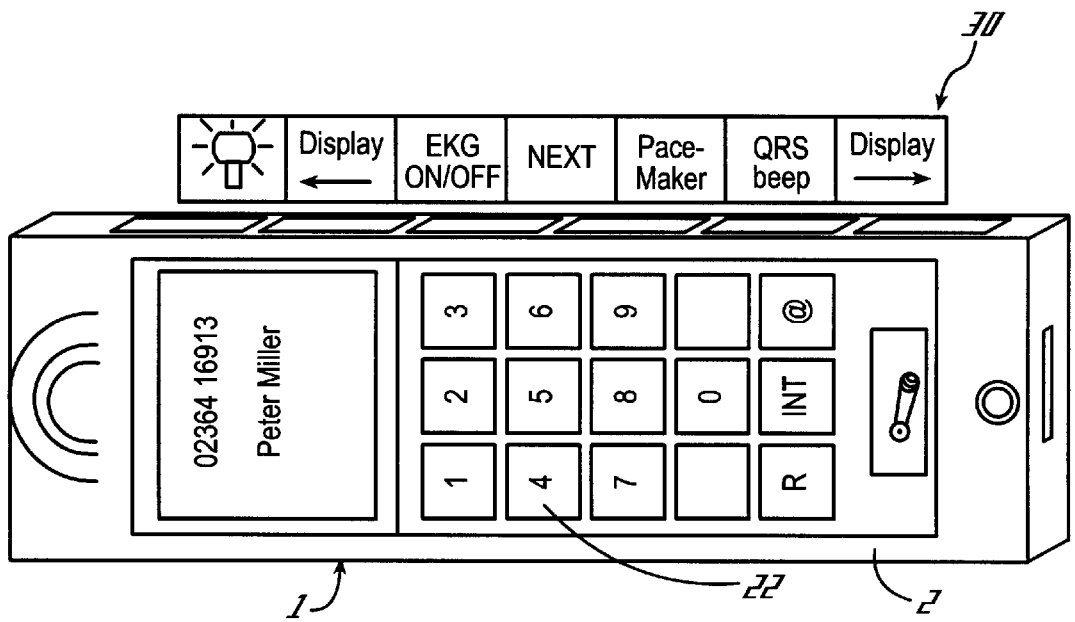
FIG. 3 shows the front of the diagnostic apparatus in accordance with the invention during radio transmission, including the display of a normal keyboard of a mobile telephone.

The display field 22 can be switched by the "EKG/ON/OFF" key, and, when the ECG function is OFF, it can represent the keyboard of a mobile telephone, see FIG. 3, which can be operated like the above explained virtual keys during the measurement operation, by depressing the keys with a pen or finger. The operation of the overall apparatus, of course, can also be designed for voice control.

Preferably, the ECG electrodes have a sensor mechanism which is able to sense the existence or absence of (skin) contact. This can also be effected during an automatic storage of the recording, as soon as the skin contact is interrupted.

Adhesive electrodes can also be attached to the electrodes.

Preferably, the apparatus is also designed for receiving messages that are written on the display field.

Figure 4:
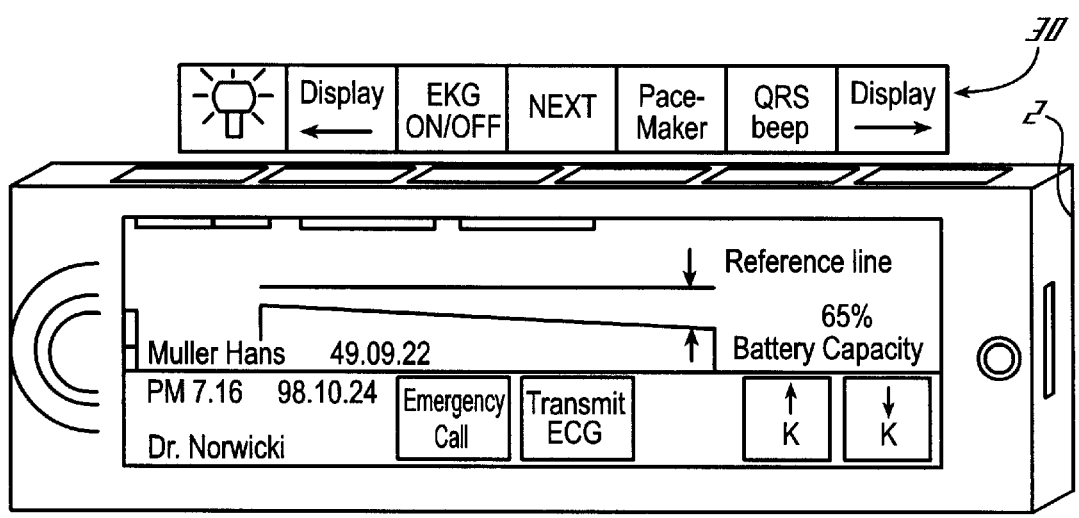
FIG. 4 shows the display field of the diagnostic apparatus checking the battery power of a pacemaker.

In the embodiment of FIG. 4, the apparatus is to be provided with an additional function designed for measuring the battery power of a pacemaker. For this purpose, a broad impulse level of the pacemaker is shown and compared with a reference line.

Also provided is an inductive scan of the pacemaker data.

Corresponding functions can be triggered by the corresponding keys shown in the display field 22, or, by the dual assignment of keys, also compare with the presentation of narrow side 30 in FIG. 4. The difference between the reference line and the curve of the pacemaker, as indicated by arrows in the display field 22, provides information on the battery charge.

What is claimed is:

1. A diagnostic apparatus, particularly a cardiac diagnostic apparatus, with a housing (2), a power supply unit provided in the housing (2), transmit-receive electronics provided at the housing (2), and electrodes (4,8,12) provided in the housing (2), for application to the body and measurement operations by recording electrical body signals, characterized in that, when activating the apparatus for recording electrical body signals the transmit function and, where appropriate, other functions not serving for measurement are disconnected.

2. A diagnostic apparatus according to claim 1, characterized in that the electrodes (4,8,12) in a first condition of the diagnostic apparatus are not uncovered, and by uncovering (5,9,13) at least one electrode (4,8,12) at least the transmit function and, where appropriate, other functions not serving for measurement are disconnected.

3. A diagnostic apparatus according to claim 1, characterized in that the electrodes are covered by an overall or individual cover, by the omission of which at least disables the transmit function and, where appropriate, other functions not serving for measurement are disconnected.

* * * * *

UNITED STATES PATENT AND TRADEMARK OFFICE
CERTIFICATE OF CORRECTION

PATENT NO.    : 6,360,118 B1
DATED         : March 19, 2002
INVENTOR(S)   : Gisela Uhlemann It is certified that error appears in the above-identified patent and that said Letters Patent is hereby corrected as shown below:

Column 1,
Line 8, "at" should read -- in --; and -- arranged at the housing -- should be inserted immediately following "electrodes".
Line 16, "mobile telephone" should read -- radio telecommunication device --.
Line 17, "cellular phone" should read -- mobile telephone --.
Line 33, "can" should read -- will --.

Column 2,
Line 52, after "upward" insert -- by a spring --.
Line 67, after the period "." insert -- The 1mV. calibration is shown at 28. --.

Column 3,
Line 19, insert -- radio -- immediately before "function".

Column 4,
Line 3, "This" should read -- Then --; and "during" should be deleted.
Line 12, "broad" should read -- broadened --.
Line 42, "omission" should read -- removal -- and "disables" should be deleted.

Signed and Sealed this

Eleventh Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,360,118 B1
DATED : March 19, 2002
INVENTOR(S) : Gisela Uhlemann

It is certified that error appears in the above-identified patent and that said Letters Patent is hereby corrected as shown below:

Column 1,
Line 45, "as" should read -- and --.
Line 53, insert -- the -- immediately following "are".
Line 55, delete "which are".

Column 2,
Lines 41 and 42, "as compared with patent application No. P" should read -- ; see DE-P --.
Line 56, "6" should read -- 10 --.

Column 3,
Line 39, "papillary" should read -- pupillary --.

Signed and Sealed this

Twelfth Day of October, 2004

JON W. DUDAS
*Director of the United States Patent and Trademark Office*